United States Patent
Qi et al.

(10) Patent No.: US 12,157,710 B2
(45) Date of Patent: Dec. 3, 2024

(54) PROCESS OF CONVERTING METHANOL IN A FLUIDIZED BED REACTOR

(71) Applicants: CHINA PETROLEUM & CHEMICAL CORPORATION, Beijing (CN); SHANGHAI RESEARCH INSTITUTE OF PETROCHEMICAL TECHNOLOGY, SINOPEC, Shanghai (CN)

(72) Inventors: Guozhen Qi, Shanghai (CN); Jing Cao, Shanghai (CN); Xiaohong Li, Shanghai (CN); Hongtao Wang, Shanghai (CN); Li Wang, Shanghai (CN); Yanxue Wang, Shanghai (CN)

(73) Assignees: CHINA PETROLEUM & CHEMICAL CORPORATION, Beijing (CN); SHANGHAI RESEARCH INSTITUTE OF PETROCHEMICAL TECHNOLOGY, SINOPEC, Shanghai (CN)

( * ) Notice: Subject to any disclaimer, the term of this patent is extended or adjusted under 35 U.S.C. 154(b) by 9 days.

(21) Appl. No.: 17/906,234

(22) PCT Filed: Mar. 12, 2021

(86) PCT No.: PCT/CN2021/080383
§ 371 (c)(1),
(2) Date: Sep. 13, 2022

(87) PCT Pub. No.: WO2021/180195
PCT Pub. Date: Sep. 16, 2021

(65) Prior Publication Data
US 2023/0118300 A1  Apr. 20, 2023

(30) Foreign Application Priority Data
Mar. 13, 2020  (CN) .......................... 202010173916.2

(51) Int. Cl.
| C07C 1/20 | (2006.01) |
| B01J 8/24 | (2006.01) |
| B01J 29/85 | (2006.01) |
| C07C 11/06 | (2006.01) |

(52) U.S. Cl.
CPC ............... *C07C 1/20* (2013.01); *B01J 8/24* (2013.01); *B01J 29/85* (2013.01); *C07C 11/06* (2013.01)

(58) Field of Classification Search
CPC ....... C07C 1/20; C07C 2529/85; C07C 11/06; C07C 11/04; B01J 8/24; B01J 8/0035; B01J 29/85; B01J 29/90; Y02P 20/584; Y02P 30/20; Y02P 30/40
USPC ........................ 585/638, 639, 640
See application file for complete search history.

(56) References Cited

U.S. PATENT DOCUMENTS

| 6,166,282 A | 12/2000 | Miller |
| 6,552,240 B1 | 4/2003 | Lattner et al. |
| 7,232,936 B1 * | 6/2007 | Yurchak .................... C07C 1/20 585/638 |
| 2003/0163010 A1 | 8/2003 | Xu et al. |
| 2014/0121434 A1 * | 5/2014 | Wei ............................ B01J 8/24 422/144 |
| 2016/0304413 A1 | 10/2016 | Liu et al. |

FOREIGN PATENT DOCUMENTS

| CN | 1404462 A | 3/2003 |
| CN | 1617842 A | 5/2005 |
| CN | 1723262 A | 1/2006 |
| CN | 101698629 A | 4/2010 |
| CN | 101811072 A | 8/2010 |
| CN | 101270020 B | 11/2011 |
| CN | 102295507 A | 12/2011 |
| CN | 101898927 B | 11/2013 |
| CN | 110452087 A | 11/2019 |
| EA | 002261 B1 | 2/2002 |
| RU | 2629354 C1 | 8/2017 |
| WO | 2013030235 A2 | 3/2013 |

(Continued)

OTHER PUBLICATIONS

Machine Translation of CN 10189827B, Nov. 6, 2013.*
International Search Report (PCT/ISA/210) with an English translation, and Written Opinion (PCT/ISA/237) mailed on Jun. 23, 2021, by the China National Intellectual Property Administration as the International Searching Authority for International Application No. PCT/CN2021/080383.
Qi et al., "Performance analysis of methanol to olefins process in fluidized bed reactor", Chemical Engineering of Oil & Gas, Dec. 31, 2013, vol. 42, Issue 3, pp. 242-247, with English abstract. (7 pages).

(Continued)

*Primary Examiner* — Colin W. Slifka
(74) *Attorney, Agent, or Firm* — Panitch Schwarze Belisario & Nadel LLP

(57) ABSTRACT

The invention relates to a process of converting methanol in a fluidized bed reactor comprising feeding a methanol-containing feedstock into a fluidized bed reactor, contacting the feedstock with a catalyst, to produce a product comprising ethylene and propylene under effective conditions; the fluidized bed reactor comprises a diluent-phase zone and a dense-phase zone, wherein the diluent-phase temperature difference between any regions of the diluent-phase zone having a methanol concentration of more than 0.1 wt % (preferably more than 0.01 wt %) in the fluidized bed reactor is controlled to be less than 20° C., and the dense-phase temperature difference between any regions in the dense-phase zone having a methanol concentration of more than 0.1 wt % (preferably more than 0.01 wt %) in the fluidized bed reactor is controlled to be less than 10° C.

16 Claims, No Drawings

(56) References Cited

FOREIGN PATENT DOCUMENTS

WO      2018/196361 A1    11/2018

OTHER PUBLICATIONS

Wang et al., "Measures to increase the production of ethylene and propylene in MTO industrial devices", Chemical Engineering & Equipment, Feb. 28, 2018, Issue 2, pp. 55-57, with English abstract. (5 pages).
Office Action issued on Sep. 2, 2023, by the Iranian Industrial Property Office (IIPO) in corresponding Iranian Patent Application No. 140150140003004543. (12 pages).
Examination Report issued Jul. 17, 2023, by the Saudi Authority for Intellectual Property (SAIP) in corresponding Saudi Patent Application No. 522440503. (8 pages).
Office Action issued on Oct. 27, 2023, by the China National Intellectual Property Administration in corresponding Chines Patent Application No. 202180020778.7 (13 pages).
Office Action issued on Oct. 20, 2023, by the Eurasian Patent Office in corresponding Eurasian Patent Application No. 202292567, with English translation of the Office Action (9 pages).
Office Action issued on Sep. 25, 2024, by the Patent Office of India in corresponding IN Application No. 202247057785, with English translation of the Office Action (6 pages).

* cited by examiner

PROCESS OF CONVERTING METHANOL IN A FLUIDIZED BED REACTOR

TECHNICAL FIELD

The present invention relates to a process for the conversion of methanol in a fluidized bed reactor.

BACKGROUND

Lower olefins comprise mainly ethylene and propylene, which are two important basic chemical raw materials. In recent years, efforts have been made to find non-petroleum sources for obtaining a product that meets the demand for these lower olefin materials. The prior art attention has largely focused on the possibility of using hydrocarbon oxygenates, particularly methanol, as the primary source of the necessary alternative feedstock. Silicoaluminophosphate molecular sieves, particularly SAPO-34 molecular sieves, exhibit relatively high product selectivities to ethylene and propylene, and lower selectivities to paraffins and C4 or more olefins in the conversion processes of methanol to olefins.

The document CN1404462A discloses a process of operating an oxygenate-to-olefin conversion reaction to provide a high amount of prime olefins. The product is provided by operating within the parameters of the desired weight hourly space velocity and oxygenate partial pressure. Operating the reaction to supply oxygenate at an oxygenate proportion index of at least 0.5, and controlling the weight hourly space velocity and the molar flow of oxygenate to the reactor to maintain a partial pressure-velocity compensation factor of at least 0.1 $psia^{-1}$ $hr^{-1}$ maintains a prime olefin selectivity of at least 45 wt %.

Document CN1723262A discloses a multi-stage riser reactor equipped with a central catalyst loop for the process of converting oxides into lower olefins, which comprises a plurality of riser reactors, a gas-solid separation zone, a plurality of shift elements, and the like, wherein each riser reactor has a port for injecting catalysts, and the separation zone separates the catalyst from the product gas. The yield of the lower olefins, calculated as carbon, in the process is generally 75-80%.

The document CN101270020B discloses a process for producing lower olefins by methanol, which comprises heating an oxygenate raw material containing methanol, and contacting the raw material with a silicoaluminophosphate molecular sieve catalyst in a reactor under the conditions of a reaction temperature of 300-600° C., a weight hourly space velocity of the oxygenate raw material of 1-50 $h^{-1}$, and a reaction pressure (gauge pressure) of 0.05-10 MPa.

However, with the increasing demand of ethylene and propylene in the market, how to improve the yield of ethylene and propylene by optimizing the reaction conditions is always a goal pursued in the art.

SUMMARY OF THE INVENTION

The inventors of the invention discover that for the process of converting methanol in a fluidized bed reactor, by controlling the temperature difference to be 20° C. or less in the area where methanol exists, particularly in the area where methanol is not converted completely, both a high conversion of the methanol and a high selectivity to lower olefins can be ensured.

The inventors of the present invention discover that controlling the temperature difference in a zone where methanol is present, particularly in a zone where the methanol concentration is relatively high, such as a dense phase zone or a fast bed zone, is more favorable for achieving high selectivity to lower olefins for a process of converting methanol in a fluidized bed reactor.

The inventors of the present invention also discover that for a process of converting methanol in a fluidized bed reactor, further controlling the temperature difference in the dilute phase zone where methanol is present, in addition to the dense phase zone described above, is more beneficial for achieving high selectivity to lower olefins.

The inventors of the present invention also discover that the amount of the mixing of catalysts having a low coke deposition amount with catalysts having a high coke deposition amount is critical to increase the olefin selectivity.

The inventors of the invention also discover that the reaction performances of the methanol raw material on the catalysts with different coke deposition amounts have great difference, and particularly, when the methanol is reacted on a catalyst with a coke deposition amount of less than 3 wt %, the selectivity to the lower olefins is greatly reduced, whilst it is necessary for the catalyst to have a coke deposition amount less than 3 wt % to ensure a high conversion of the raw material.

The inventors of the present invention also discover that after the regenerated catalysts are returned from the regenerator to the fluidized bed reactor, a good distribution of the regenerated catalysts within the reactor is critical. This portion of the catalysts affects not only the average coke deposition amount in the reactor, but also the temperature profile of the reactor. When the methanol raw material contacts with the high-temperature and high-activity regenerated catalyst, the selectivity to olefins can be greatly reduced. When the regenerated catalysts are not distributed uniformly, the temperature within the reactor will be not uniform accordingly, which also affects the selectivity to olefin.

The present invention has been completed based on these discoveries.

Specifically, the present invention provides, for example, embodiments of:

1. A process of converting methanol in a fluidized bed reactor, comprising: feeding a methanol-containing feedstock into a fluidized bed reactor, and contacting the feedstock with a catalyst, to produce a product comprising ethylene and propylene under effective conditions; the fluidized bed reactor comprises a diluent-phase zone and a dense-phase zone, characterized in that the diluent-phase temperature difference between any regions of the diluent-phase zone having a methanol concentration of more than 0.1 wt % (preferably more than 0.01 wt %) in the fluidized bed reactor is controlled to be less than 20° C., and the dense-phase temperature difference between any regions in the dense-phase zone having a methanol concentration of more than 0.1 wt % (preferably more than 0.01 wt %) in the fluidized bed reactor is controlled to be less than 10° C.

2. The process of embodiment 1, characterized in that the dilute-phase temperature difference in the fluidized bed reactor is less than 10° C. and/or the dense-phase temperature difference in the fluidized bed reactor is less than 10° C.

3. The process according to any one of embodiments 1-2, characterized in that the effective conditions comprise: the catalysts in the regions having a methanol concentration of more than 0.01 wt % in the fluidized bed reactor have a coke deposition amount of 1.5-10 wt %, preferably 2-8 wt %, more preferably 4-7 wt %, calculated as the weight of molecular sieve in the catalyst.

4. The process according to embodiment 3, characterized in that in the regions having a methanol concentration of more than 0.01 wt % in the fluidized bed reactor, the catalysts having a coke deposition mount of less than 3 wt % account, calculated as the weight of the molecular sieve in the catalyst, for 1 to 20 wt %, preferably 1.5 to 10 wt %, more preferably 2 to 5 wt %, based on the total weight of the catalysts in the fluidized bed reactor.

5. The process of embodiment 4, characterized in that in the regions having a methanol concentration of more than 0.01 wt % in the fluidized bed reactor, calculated as the weight of the molecular sieve in the catalyst, the catalysts having a coke deposition of from 3 wt % to less than 5 wt % account for 10 to 70 wt %, preferably 15 to 60 wt %, 20 to 50 wt %, or 30 to 45 wt %; and the catalysts having a coke deposition amount of from 5 wt % to 10 wt % account for 10 to 88 wt %, preferably 15 to 80 wt %, 20 to 70 wt %, or 30 to 60 wt %.

6. The process according to any one of the preceding embodiments, characterized in that the effective conditions comprise: a reaction temperature of 400-550° C., and a reaction pressure of 0-1 MPa.

7. The process according to any one of the preceding embodiments, wherein the spent catalyst is derived from deactivation of the catalyst in the reaction zone, the spent catalyst is introduced into a regenerator through a spent inclined line to be regenerated to form a regenerated catalyst, and the regenerated catalyst is returned to the fluidized bed reaction zone through a regeneration inclined line; characterized in that the difference of the coke deposition amounts between the spent catalyst and the regenerated catalyst is less than 7 wt %, preferably less than 6 wt %, more preferably less than 4 wt %.

8. The process of any of the preceding embodiments, characterized in that the active component of the catalyst is a silicoaluminophosphate molecular sieve; wherein the silicoaluminophosphate molecular sieve is SAPO-18, SAPO-34, SAPO-5 or a combination thereof, preferably SAPO-34; and/or the fluidized bed reactor is in the form of a dense phase bed, turbulent bed, or fast fluidized bed.

9. The process according to any one of the preceding embodiments, characterized in that a temperature regulation device is equipped inside and/or outside the fluidized bed reactor.

10. The process according to any one of the preceding embodiments, characterized in that the lower portion of the reaction zone is equipped with a regeneration inclined line outlet, the regeneration inclined line outlet is equipped with a catalyst distributor, and the catalyst distributor is substantially horizontally arranged along the radial direction of the reaction zone.

11. The process of embodiment 10, characterized in that the delivering medium within the catalyst distributor is at least one selected from steam, oxygenate byproducts, and C4 hydrocarbons; where the oxygenate byproducts comprise acetone and acetaldehyde.

TECHNICAL EFFECTS

According to the process of the present invention, not only high conversion of raw materials can be ensured, but also high selectivity to the lower olefins can be ensured.

EMBODIMENTS OF THE INVENTION

The present invention will be further illustrated in more detail below, while it should be understood that the scope of the invention is not restricted by the embodiments, but is defined by the appended claims.

All publications, patent applications, patents, and other references mentioned in this specification are herein incorporated by reference in their entirety. Unless defined specifically, all technical and scientific terms used herein have the same meaning as commonly understood by those skilled in the art to which this invention belongs. In case of conflict, the present specification, including definitions, will control.

When the present specification mentions a material, substance, method, step, device, or component, etc. with the derivative words "known to those skilled in the art", "prior art" or the like, the term derived is intended to cover those conventionally used in the field of the present application, but also cover those that are not currently known, whilst will become known in the art to be useful for the similar purposes.

In the context of this specification, the methods for preparing SAPO molecular sieves or SAPO molecular sieve catalysts are well known in the art.

In the context of the present specification, the coke deposition amount of the catalysts in the reaction zone is actually an average value. This is because, in a fluidized bed reactor, a catalyst circulation between reaction and regeneration exists, resulting in catalysts having a low coke deposition amount and catalysts having a high coke deposition amount, such that the mixing of multiple strands of catalysts is inevitably existing.

In the context of this specification, the coke deposition amount (or average coke deposition amount) of the catalyst is calculated by the weight of coke deposit on the catalyst divided by the weight of the catalyst. The method for measuring the weight of the coke deposit on the catalyst comprises the following steps: weighing 0.1-1 g of the carbon-carrying catalyst, placing the catalyst in a high-temperature carbon analyzer for combustion, and measuring the weight of carbon dioxide generated by combustion through infrared rays, to provide the weight of coke deposit on the catalyst. In order to determine the coke deposition amount of the catalyst in the reaction zone, aliquots of the catalyst in small equal amounts may be withdrawn continuously or periodically from various locations in the reaction zone.

All percentages, parts, ratios, etc. involved in this specification are indicated by weight and pressures are gauge pressures unless explicitly indicated otherwise.

In the context of this specification, any two or more embodiments of the invention may be combined to form an embodiment, and the resulting embodiment is a part of the original disclosure of this specification, and is within the protection scope of the invention.

Example 1

A methanol raw material (with a methanol purity of 95 wt %) was fed into the reaction zone of a fast fluidized bed (called as fluidized bed reaction zone hereinafter), and contacted with a SAPO-34 molecular sieve catalyst, generating a product containing ethylene and propylene under effective conditions. The catalyst in the fluidized bed reaction zone was inactivated to form a spent catalyst, which spent catalyst was fed into a regenerator to be regenerated to form a regenerated catalyst, which regenerated catalyst was returned to the fluidized bed reaction zone. The difference between the coke deposition amounts of the spent catalyst and the regenerated catalyst was 5 wt %. The gas phase and the catalyst in the fluidized bed reaction zone were rapidly separated through the separation device subsequent to the reaction or after leaving the fluidized bed reaction zone. The effective conditions comprised: a reaction temperature of 450° C., a reaction gauge pressure of 0.15 MPa, and calculated as the weight of the molecular sieve on the catalyst, in the fluidized bed reactor, any regions having a methanol concentration of more than 0.1 wt % in the fluidized bed reactor had a temperature difference of 4° C., and a catalyst coke deposition of 1.5 wt %, wherein the catalyst having a coke deposition amount of less than 3 wt % accounted for 2 wt %, the catalyst having a coke deposition amount of from 3 wt % to less than 5 wt % accounted for 68 wt %, and the catalyst having a coke deposition amount from 5 wt % to 10 wt % accounted for 23 wt %, based on the total catalyst in the fluidized bed reactor. The outlet of the regeneration inclined line was equipped with a catalyst distributor, which catalyst distributor was horizontally arranged along the radial direction of the fluidized bed reactor, to uniformly distribute the regenerated catalyst on the radial plane of the fluidized bed reactor reaction zone. The delivering medium in the catalyst distributor was steam. The sampling analysis results showed that the conversion of methanol was 99.98% and the selectivity to ethylene+propylene on carbon basis was 83.07%.

Example 2

A methanol raw material (with a methanol purity of 95 wt %) was fed into the fast fluidized bed reaction zone, contacted an SAPO-34 molecular sieve catalyst, generating a product containing ethylene and propylene under effective conditions. The catalyst in the fluidized bed reaction zone was inactivated to form a spent catalyst, which spent catalyst was fed into a regenerator to be regenerated to form a regenerated catalyst, which regenerated catalyst was returned to the fluidized bed reaction zone. The difference between the coke deposition amounts of the spent catalyst and the regenerated catalyst was 5 wt %. The gas phase and the catalyst in the fluidized bed reaction zone were rapidly separated through the separation device subsequent to the reaction or after leaving the fluidized bed reaction zone. The effective conditions comprised: a reaction temperature of 450° C., a reaction gauge pressure of 0.15 MPa, and calculated as the weight of the molecular sieve on the catalyst, in the fluidized bed reactor, any regions having a methanol concentration of more than 0.1 wt % in the fluidized bed reactor had a temperature difference of 4° C., and a catalyst coke deposition of 5.5 wt %, wherein the catalyst having a coke deposition amount of less than 3 wt % accounted for 10 wt %, the catalyst having a coke deposition amount of from 3 wt % to less than 5 wt % accounted for 50 wt %, and the catalyst having a coke deposition amount from 5 wt % to 10 wt % accounted for 35 wt %, based on the total catalyst in the fluidized bed reactor. The outlet of the regeneration inclined line was equipped with a catalyst distributor, which catalyst distributor was horizontally arranged along the radial direction of the fluidized bed reactor, to uniformly distribute the regenerated catalyst on the radial plane of the fluidized bed reactor reaction zone. The delivering medium in the catalyst distributor was steam. The sampling analysis results showed that the conversion of methanol was 99.95% and the selectivity to ethylene+propylene on carbon basis was 84.13%.

Example 3

A methanol raw material (with a methanol purity of 95 wt %) was fed into the fast fluidized bed reaction zone, contacted an SAPO-34 molecular sieve catalyst, generating a product containing ethylene and propylene under effective conditions. The catalyst in the fluidized bed reaction zone was inactivated to form a spent catalyst, which spent catalyst was fed into a regenerator to be regenerated to form a regenerated catalyst, which regenerated catalyst was returned to the fluidized bed reaction zone. The difference between the coke deposition amounts of the spent catalyst and the regenerated catalyst was 5 wt %. The gas phase and the catalyst in the fluidized bed reaction zone were rapidly separated through the separation device subsequent to the reaction or after leaving the fluidized bed reaction zone. The effective conditions comprised: a reaction temperature of 400° C., a reaction gauge pressure of 0.05 MPa, and calculated as the weight of the molecular sieve on the catalyst, in the fluidized bed reactor, any regions having a methanol concentration of more than 0.1 wt % in the fluidized bed reactor had a temperature difference of 9° C., and a catalyst coke deposition of 1.5 wt %, wherein the catalyst having a coke deposition amount of less than 3 wt % accounted for 1.5 wt %, the catalyst having a coke deposition amount of from 3 wt % to less than 5 wt % accounted for 43 wt %, and the catalyst having a coke deposition amount from 5 wt % to 10 wt % accounted for 53 wt %, based on the total catalyst in the fluidized bed reactor. The outlet of the regeneration inclined line was equipped with a catalyst distributor, which catalyst distributor was horizontally arranged along the radial direction of the fluidized bed reactor, to uniformly distribute the regenerated catalyst on the radial plane of the fluidized bed reactor reaction zone. The delivering medium in the catalyst distributor was steam. The sampling analysis results showed that the conversion of methanol was 99.06% and the selectivity to ethylene+propylene on carbon basis was 82.56%.

Example 4

A methanol raw material (with a methanol purity of 95 wt %) was fed into the fast fluidized bed reaction zone, contacted an SAPO-34 molecular sieve catalyst, generating a product containing ethylene and propylene under effective conditions. The catalyst in the fluidized bed reaction zone was inactivated to form a spent catalyst, which spent catalyst was fed into a regenerator to be regenerated to form a regenerated catalyst, which regenerated catalyst was returned to the fluidized bed reaction zone. The difference between the coke deposition amounts of the spent catalyst and the regenerated catalyst was 6 wt %. The gas phase and the catalyst in the fluidized bed reaction zone were rapidly separated through the separation device subsequent to the reaction or after leaving the fluidized bed reaction zone. The effective conditions comprised: a reaction temperature of 550° C., a reaction gauge pressure of 1.0 MPa, and calculated as the weight of the molecular sieve on the catalyst, in the fluidized bed reactor, any regions having a methanol concentration of more than 0.1 wt % in the fluidized bed reactor had a temperature difference of 9° C., and a catalyst coke deposition of 8 wt %, wherein the catalyst having a coke deposition amount of less than 3 wt % accounted for 18 wt %, the catalyst having a coke deposition amount of from 3 wt % to less than 5 wt % accounted for 30 wt %, and the catalyst having a coke deposition amount from 5 wt % to 10 wt % accounted for 48 wt %, based on the total catalyst in the fluidized bed reactor. The outlet of the regeneration inclined line was equipped with a catalyst distributor, which catalyst distributor was horizontally arranged along the radial direction of the fluidized bed reactor, to uniformly distribute the regenerated catalyst on the radial plane of the fluidized bed reactor reaction zone. The delivering medium in the catalyst distributor was C4. The sampling analysis results showed that the conversion of methanol was 99.99% and the selectivity to ethylene+propylene on carbon basis was 85.44%.

Example 5

A methanol raw material (with a methanol purity of 95 wt %) was fed into the reaction zone of a turbulent fluidized bed, and contacted with a SAPO-34 molecular sieve catalyst, generating a product containing ethylene and propylene under effective conditions. The catalyst in the fluidized bed reaction zone was inactivated to form a spent catalyst, which spent catalyst was fed into a regenerator to be regenerated to form a regenerated catalyst, which regenerated catalyst was returned to the fluidized bed reaction zone. The difference between the coke deposition amounts of the spent catalyst and the regenerated catalyst was 5 wt %. The gas phase and the catalyst in the fluidized bed reaction zone were rapidly separated through the separation device subsequent to the reaction or after leaving the fluidized bed reaction zone. The effective conditions comprised: a reaction temperature of 480° C., a reaction gauge pressure of 0.15 MPa, and calculated as the weight of the molecular sieve on the catalyst, in the fluidized bed reactor, any regions having a methanol concentration of more than 0.1 wt % in the fluidized bed reactor had a temperature difference of 2° C., and a catalyst coke deposition of 4.5 wt %, wherein the catalyst having a coke deposition amount of less than 3 wt % accounted for 5 wt %, the catalyst having a coke deposition amount of from 3 wt % to less than 5 wt % accounted for 65 wt %, and the catalyst having a coke deposition amount from 5 wt % to 10 wt % accounted for 25 wt %, based on the total catalyst in the fluidized bed reactor. The outlet of the regeneration inclined line was equipped with a catalyst distributor, which catalyst distributor was horizontally arranged along the radial direction of the fluidized bed reactor, to uniformly distribute the regenerated catalyst on the radial plane of the fluidized bed reactor reaction zone. The delivering medium in the catalyst distributor was an oxygenate by-product. The sampling analysis results showed that the conversion of methanol was 99.93% and the selectivity to ethylene+propylene on carbon basis was 84.09%.

Comparative Example 1

The conditions and procedures described in Example 5 were followed except that any regions having a methanol concentration of more than 0.1 wt % in the fluidized bed reactor had a temperature difference of 22° C. The sampling analysis results showed that the conversion of methanol was 99.74% and the selectivity to ethylene+propylene on carbon basis was 81.17%.

Comparative Example 2

The conditions and procedures described in Examples 5 were followed except that any regions having a methanol concentration of more than 0.1 wt % in the fluidized bed reactor had a temperature difference of 27° C. The sampling analysis results showed that the conversion of methanol was 99.33% and the selectivity to ethylene+propylene on carbon basis was 80.55%).

Obviously, the process according to the present invention could achieve the purpose of improving the yield of the lower olefins and thus was able to be used for the industrial production of the lower olefins.

The invention claimed is:

1. A process of converting methanol in a fluidized bed reactor comprising feeding a methanol-containing feedstock into a fluidized bed reactor, and contacting the feedstock with a catalyst, to produce a product comprising ethylene and propylene under effective conditions; wherein the fluidized bed reactor comprises a diluent-phase zone and a dense-phase zone, wherein the diluent-phase temperature difference between any regions of the diluent-phase zone having a methanol concentration of more than 0.1 wt % in the fluidized bed reactor is controlled to be less than 20° C., and the dense-phase temperature difference between any regions in the dense-phase zone having a methanol concentration of more than 0.1 wt % in the fluidized bed reactor is controlled to be less than 10° C.

2. The process according to claim 1, wherein the diluent-phase temperature difference in the fluidized bed reactor is less than 10° C. and/or the dense-phase temperature difference in the fluidized bed reactor is less than 10° C.

3. The process according to claim 1, wherein the effective conditions comprise: the catalyst in the regions having a methanol concentration of more than 0.01 wt % in the fluidized bed reactor has a coke deposition amount of 1.5-10 wt %, calculated as the weight of molecular sieve in the catalyst.

4. The process according to claim 3, wherein in the regions having a methanol concentration of more than 0.01 wt % in the fluidized bed reactor, the catalyst having a coke deposition amount of less than 3 wt %, calculated as the weight of the molecular sieve in the catalyst, accounts for 1 to 20 wt %, based on the total weight of the catalysts-catalyst in the fluidized bed reactor.

5. The process according to claim 4, wherein in the regions having a methanol concentration of more than 0.01 wt % in the fluidized bed reactor, calculated as the weight of the molecular sieve in the catalyst, the catalyst having a coke deposition of from 3 wt % to less than 5 wt % accounts for 10 to 70 wt %, based on the total weight of the catalyst in the fluidized bed reactor; and the catalyst having a coke deposition amount of from 5 wt % to 10 wt % accounts for 10 to 88 wt %, based on the total weight of the catalyst in the fluidized bed reactor.

6. The process according to claim 5, wherein in the regions having a methanol concentration of more than 0.01 wt % in the fluidized bed reactor, calculated as the weight of the molecular sieve in the catalyst, the catalyst having a coke deposition of from 3 wt % to less than 5 wt % accounts for 30 to 45 wt %, based on the total weight of the catalyst in the fluidized bed reactor; and the catalyst having a coke deposition amount of from 5 wt % to 10 wt % accounts for 30 to 60 wt %, based on the total weight of the catalyst in the fluidized bed reactor.

7. The process according to claim 4, wherein in the regions having a methanol concentration of more than 0.01 wt % in the fluidized bed reactor, the catalyst having a coke deposition amount of less than 3 wt %, calculated as the weight of the molecular sieve in the catalyst, accounts for 2 to 5 wt %, based on the total weight of the catalyst in the fluidized bed reactor.

8. The process according to claim 3, wherein the effective conditions comprise: the catalyst in the regions having a methanol concentration of more than 0.01 wt % in the fluidized bed reactor has a coke deposition amount of 4-7 wt %, calculated as the weight of molecular sieve in the catalyst.

9. The process according to claim 1, wherein the effective conditions comprise: a reaction temperature of 400-550° C., and a reaction pressure of 0-1 MPa.

10. The process according to claim 1, wherein the catalyst in the fluidized bed reactor is deactivated to form a spent catalyst, the spent catalyst is introduced into a regenerator through a spent inclined line to be regenerated to form a regenerated catalyst, and the regenerated catalyst is returned to the fluidized bed reactor through a regeneration inclined line; wherein the difference of the coke deposition amounts between the spent catalyst and the regenerated catalyst is less than 7 wt %.

11. The process according to claim 10, wherein the difference of the coke deposition amounts between the spent catalyst and the regenerated catalyst is less than 4 wt %.

12. The process of claim 1, wherein an active component silicoaluminophosphate molecular sieve; wherein the of the catalyst is a silicoaluminophosphate molecular sieve is SAPO-18, SAPO-34, SAPO-5 or a combination thereof; and/or the fluidized bed reactor is in the form of a dense phase bed, turbulent bed, or fast fluidized bed.

13. The process according to claim 1, wherein a temperature regulation device is equipped inside and/or outside the fluidized bed reactor.

14. The process according to claim 1, wherein a lower portion of the fluidized bed reactor is equipped with a regeneration inclined line outlet, the regeneration inclined line outlet is equipped with a catalyst distributor, and the catalyst distributor is substantially horizontally arranged along the radial direction of the fluidized bed reactor.

15. The process according to claim 14, wherein a delivering medium within the catalyst distributor is at least one selected from steam, oxygenate byproducts, and C4 hydrocarbons; where the oxygenate byproducts comprise acetone and acetaldehyde.

16. The process according to claim 1, wherein the diluent-phase temperature difference between any regions of the diluent-phase zone having a methanol concentration of more than 0.01 wt % in the fluidized bed reactor is controlled to be less than 20° C., and the dense-phase temperature difference between any regions in the dense-phase zone having a methanol concentration of more than 0.01 wt % in the fluidized bed reactor is controlled to be less than 10° C.

* * * * *